(12) United States Patent
Kwak

(10) Patent No.: US 7,695,514 B2
(45) Date of Patent: Apr. 13, 2010

(54) FACET JOINT AND SPINAL LIGAMENT REPLACEMENT

(75) Inventor: Seungkyu Daniel Kwak, Grafton, MA (US)

(73) Assignee: DePuy Spine, Inc., Raynham, MA (US)

( * ) Notice: Subject to any disclaimer, the term of this patent is extended or adjusted under 35 U.S.C. 154(b) by 744 days.

(21) Appl. No.: 11/321,905

(22) Filed: Dec. 29, 2005

(65) Prior Publication Data

US 2007/0156237 A1 Jul. 5, 2007

(51) Int. Cl.
*A61F 2/44* (2006.01)
*A61F 2/08* (2006.01)
*A61B 17/70* (2006.01)

(52) U.S. Cl. .................. 623/17.11; 623/13.14; 606/247; 606/249

(58) Field of Classification Search .............. 623/13.14, 623/17.11, 17.16; 606/247–249, 279
See application file for complete search history.

(56) References Cited

U.S. PATENT DOCUMENTS

| | | | |
|---|---|---|---|
| 5,571,191 A | 11/1996 | Fitz | |
| 6,132,464 A | 10/2000 | Martin | |
| 6,419,703 B1 | 7/2002 | Fallin et al. | |
| 6,565,605 B2 | 5/2003 | Goble et al. | |
| 6,579,319 B2 | 6/2003 | Goble et al. | |
| 6,610,091 B1 | 8/2003 | Reiley | |
| 6,669,729 B2 | 12/2003 | Chin | |
| 6,902,580 B2 | 6/2005 | Fallin et al. | |
| 2002/0123806 A1 | 9/2002 | Reiley | |
| 2003/0004572 A1 | 1/2003 | Goble et al. | |
| 2003/0028250 A1 | 2/2003 | Reiley et al. | |
| 2003/0040797 A1 | 2/2003 | Fallin et al. | |
| 2003/0171750 A1 | 9/2003 | Chin | |
| 2003/0191532 A1 | 10/2003 | Goble et al. | |
| 2004/0006391 A1 | 1/2004 | Reiley | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0111154 A1 | 6/2004 | Reiley | |
| 2004/0127989 A1* | 7/2004 | Dooris et al. | 623/13.17 |
| 2004/0254575 A1 | 12/2004 | Obenchain et al. | |
| 2005/0027361 A1 | 2/2005 | Reiley | |
| 2005/0033434 A1 | 2/2005 | Berry | |
| 2005/0055096 A1 | 3/2005 | Serhan et al. | |
| 2005/0085912 A1 | 4/2005 | Arnin et al. | |
| 2005/0102028 A1 | 5/2005 | Arnin et al. | |
| 2005/0119748 A1 | 6/2005 | Reiley et al. | |
| 2006/0052785 A1* | 3/2006 | Augostino et al. | 606/61 |
| 2006/0149229 A1 | 7/2006 | Kwak et al. | |
| 2007/0005137 A1 | 1/2007 | Kwak | |

* cited by examiner

*Primary Examiner*—Thomas J Sweet
*Assistant Examiner*—Yashita Sharma
(74) *Attorney, Agent, or Firm*—Nutter McClennan & Fish LLP

(57) ABSTRACT

An implantable device for stabilizing at least a portion of a spinal column. The implantable device comprises an implantable artificial facet joint and one or more artificial ligaments connecting the implanted artificial facet joint to a third vertebra disposed adjacent to either the first or the second vertebra. The artificial facet joint, when implanted, spans a first vertebra and a second vertebra, adjacent to the first vertebra.

26 Claims, 8 Drawing Sheets

FACET JOINT AND SPINAL LIGAMENT REPLACEMENT

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Each joint is surrounded by a capsule of connective tissue and produces a fluid to nourish and lubricate the joint. The joint surfaces are coated with cartilage allowing the joints to move or articulate relative to one another.

Diseased, degenerated, or otherwise impaired facet joints and/or discs can be surgically removed and prosthetic discs and/or facet joints implanted to restore natural function of a spine. Similar surgery may also be required after a laminectomy (removal of lamina), since a laminectomy predisposes the patient to instability and may lead to post-laminectomy kyphosis (abnormal forward curvature of the spine), pain, and neurological dysfunction.

However, implantation of an artificial facet joint frequently requires removal of a significant portion of the posterior ligamentous structures of the spine. This results in incomplete restoration of natural function of a spine as well as decreased stability and increased mobility (increased range of motion) of the patient's spinal column. Accordingly, there is a need for an artificial facet joint that would restore the natural function of a spine, including that of posterior ligaments.

SUMMARY OF THE INVENTION

The present invention is an implantable device, kit, and related methods for replacing or augmenting facet joints and spinal ligamentous structures. The device of the present invention includes an artificial facet joint that restore the function of diseased, degenerated, or otherwise impaired facet joint. The device also includes artificial ligaments that restore the functions of spinal ligamentous structures resected during the implantation of the artificial facet joint. Particularly, when implantation of artificial facet joint requires the removal of spinous process or the removal of both lamina and spinous process, the ligamentous structures that attach to the spinous process and lamina are also resected. Therefore, device of the present invention includes artificial ligaments to restore functions of any spinal ligaments removed during the implantation of the artificial facet joint.

In one embodiment, the present invention is an implantable device for stabilizing at least a portion of a spinal column. The implantable device comprises one or more implantable artificial facet joints and one or more artificial ligaments. The artificial facet joint replaces or augments the function of the diseased facet joint or joints, and when implanted, it spans a first vertebra and a second vertebra adjacent to the first vertebra. The artificial ligaments replace any spinal ligaments resected during the implantation of the artificial facet. The artificial ligaments span between the first and second vertebrae coupled by the facet joint, and the artificial ligaments span between a third vertebra and either of the first or the second vertebra coupled by the facet joint. The ends of an artificial ligament can couple to the vertebra, or the ends may couple to the facet joint replacement.

In another embodiment, the present invention is a kit for restoring the function of a spinal segment. The kit comprises components to assemble at least one artificial facet joint and at least one artificial ligament. The artificial facet joint, when implanted, spans a first vertebra, and a second vertebra adjacent to the first vertebra. The artificial ligament spans the first and second vertebrae coupled by the artificial facet joint. Additionally or alternatively, the artificial ligament span a third vertebra and either of the first or the second vertebra coupled by the artificial facet joint. The kit may also include multiple sizes and orientations of artificial facet joints and artificial ligaments to accommodate various patient anatomies and sizes.

In another embodiment, the present invention is a method of restoring the function of a spinal segment. The method comprises the step of connecting at least one artificial ligament between a third vertebra and either of the first or a second vertebra coupled by the artificial facet joint. Alternatively, the method comprises the step of connecting at least one artificial ligament between an artificial facet joint, said artificial joint spanning a first and a second adjacent vertebrae, and a third vertebra disposed adjacent to the first or the second vertebra.

A device, a kit and a method of the present invention advantageously restores natural mobility and stiffness of a spinal segment by introducing an artificial facet joint and ligament device that restores connection between two adjacent vertebrae coupled by facet joints and connection between a third vertebra and either of the two vertebrae coupled by the artificial facet joint.

DETAILED DESCRIPTION OF THE INVENTION

Figure 1:
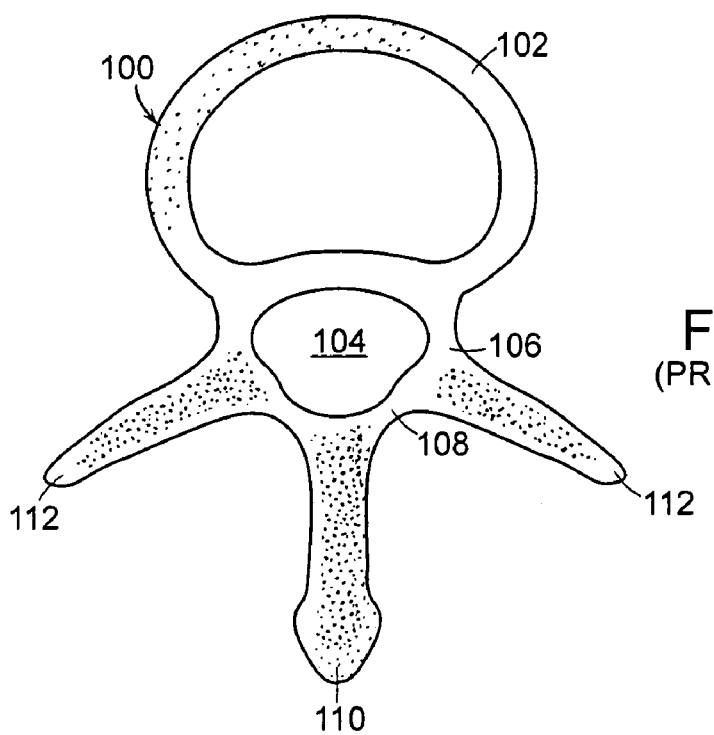
FIG. 1 is a schematic cross-section of a representative vertebra.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Referring to FIG. 1, a cross-section of a representative vertebra is shown. Vertebra 100 includes vertebra body 102, spinal canal 104, pedicle 106, lamina 108, spinous process 110 and transverse processes 112.

Figure 2A:
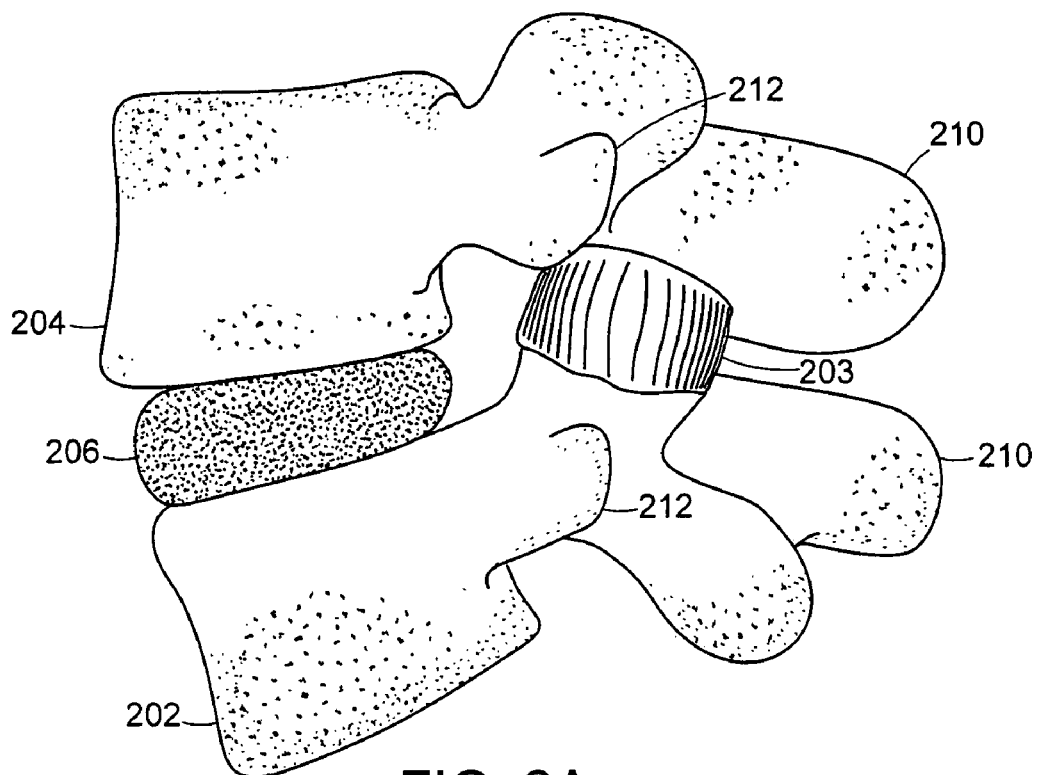
FIG. 2A is a side view of a functional spinal unit (FSU).
Figure 2B:
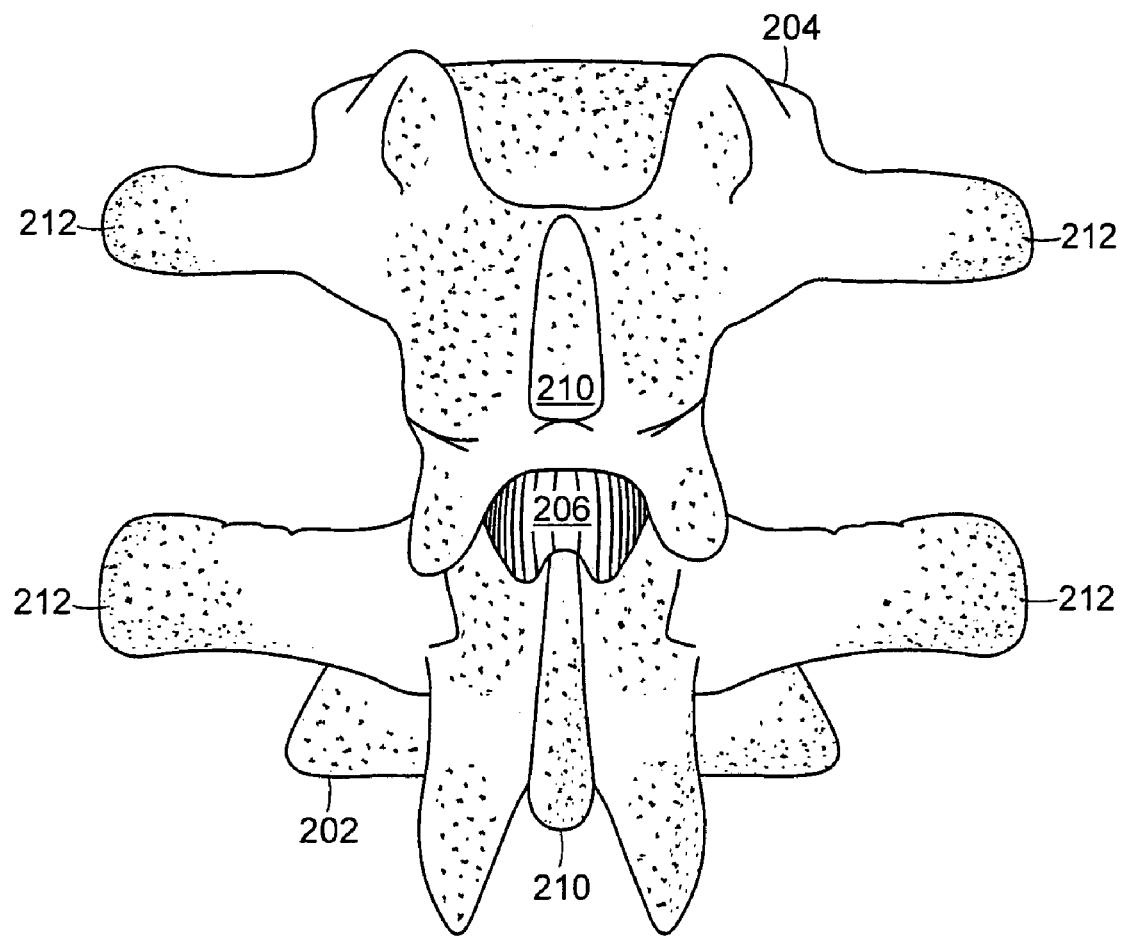
FIG. 2B is a posterior view, respectively, of a functional spinal unit (FSU).

FIGS. 2A and 2B depict a side view and a posterior view, respectively, of a functional spinal unit (FSU). An FSU comprises inferior vertebra 202 and superior vertebra 204 connected by intervertebral disk 206, facet joints 208(located inside the facet joint capsule), and all ligaments (not shown) connecting inferior vertebra 202 and superior vertebra 204. Vertebrae 202 and 204 include posterior-facing spinous processes 210 and laterally facing transverse processes 212.

Figure 3:
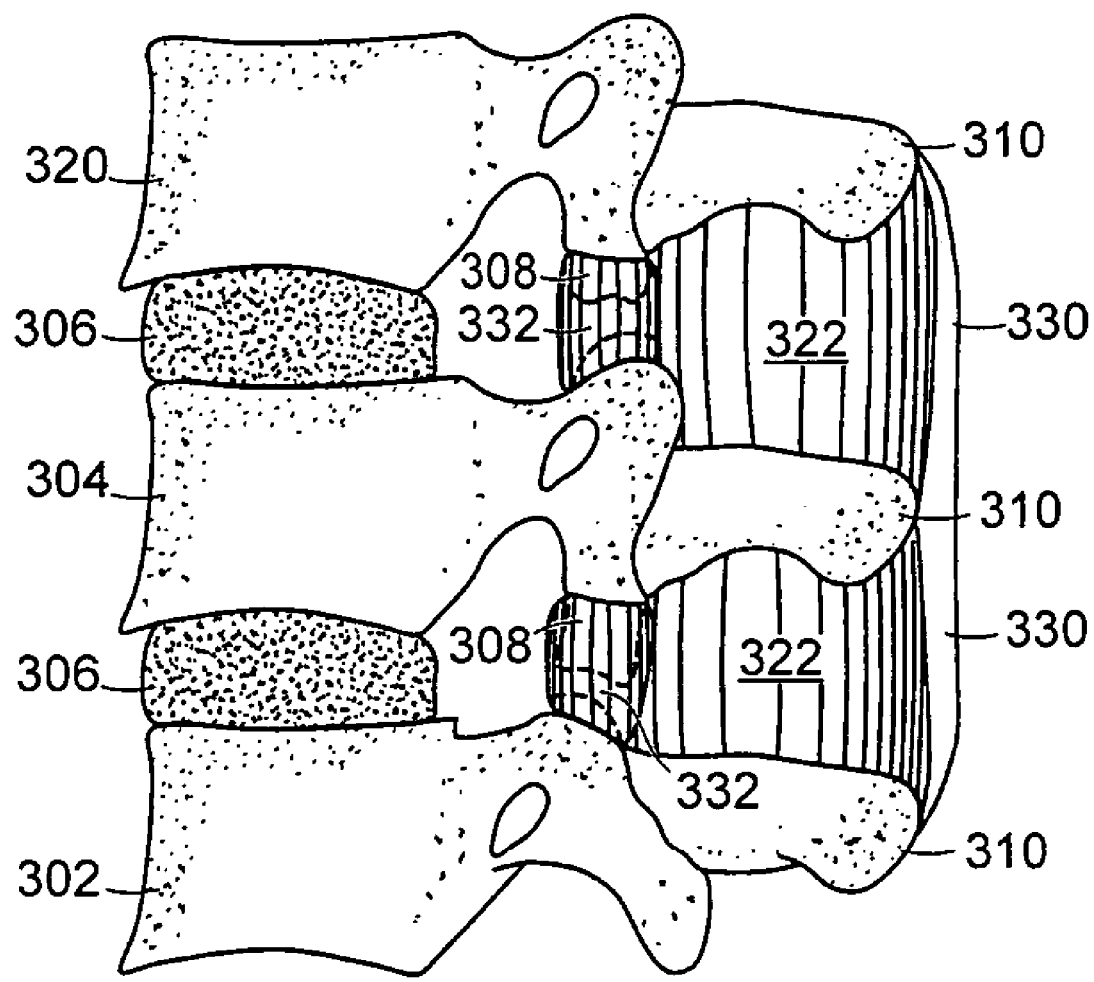
FIG. 3 is a side view of portion of a spinal column that includes three sequential vertebrae.

Referring to FIG. 3, vertebra 320, superior and adjacent to vertebra 304, is shown. In addition to intervertebral disks 306 and facet joints 308 (located inside the facet joint capsule and capsulary ligament 332), various ligaments provide further support to a spinal column. Of all spinal ligaments, the particular ligaments of related to this invention are ligamentum flavum (not shown), interspinous ligament (not shown), supraspinous ligament 330, and facet capsulary ligament 332.

Figure 4A:
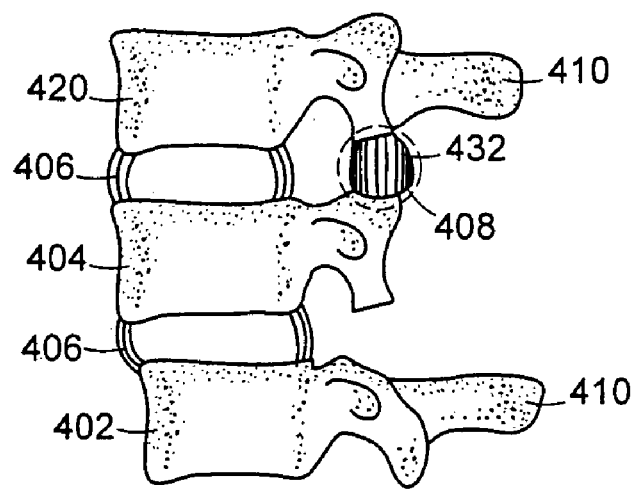
FIGS. 4A and 4B are a side view and a posterior view, respectively, of three sequential vertebrae following a facetectomy (removal of facet joints) and laminectomy (removal of lamina and spinous process).
Figure 4B:
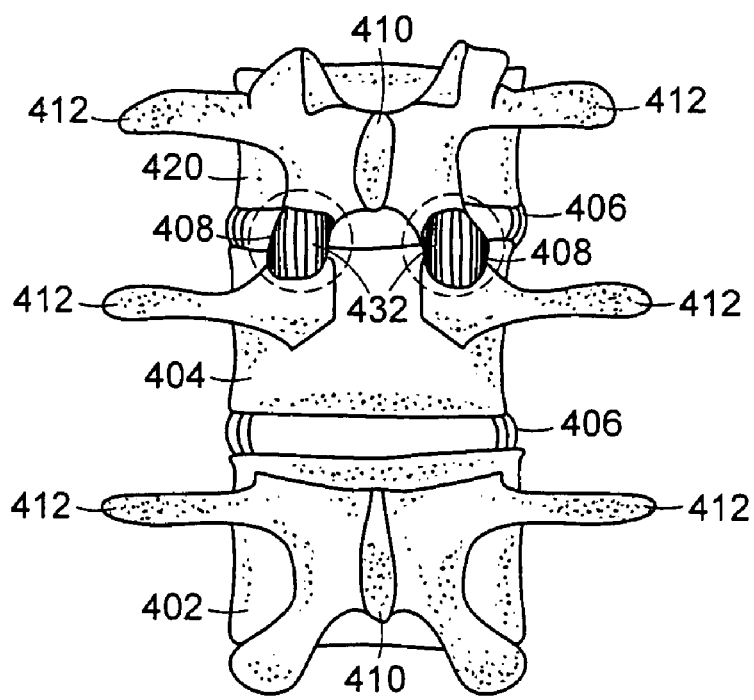

FIGS. 4A and 4B depict lateral and posterior views, respectively, of three sequential vertebrae following a facetectomy (removal of facet joints 408) between vertebrae 402 and 404 and laminectomy (removal of lamina and spinous process) on vertebra 404. As can be seen, vertebra 404 lacks spinous process 410. Vertebrae 402 and 404 are no longer coupled by facet joints 408. Facet joints 408 are intact between vertebra 404 and 420. With reference to FIGS. 4A and 4B, and by comparison to FIG. 3, vertebrae 402 and 404 are no longer connected, such as are 404 and 420, by capsulary ligaments 432, interspinous ligament 422, and supraspinous ligament 430. Also, vertebrae 404 and 420 are no longer connected by an interspinous ligament and a supraspinous ligament.

Figure 5:
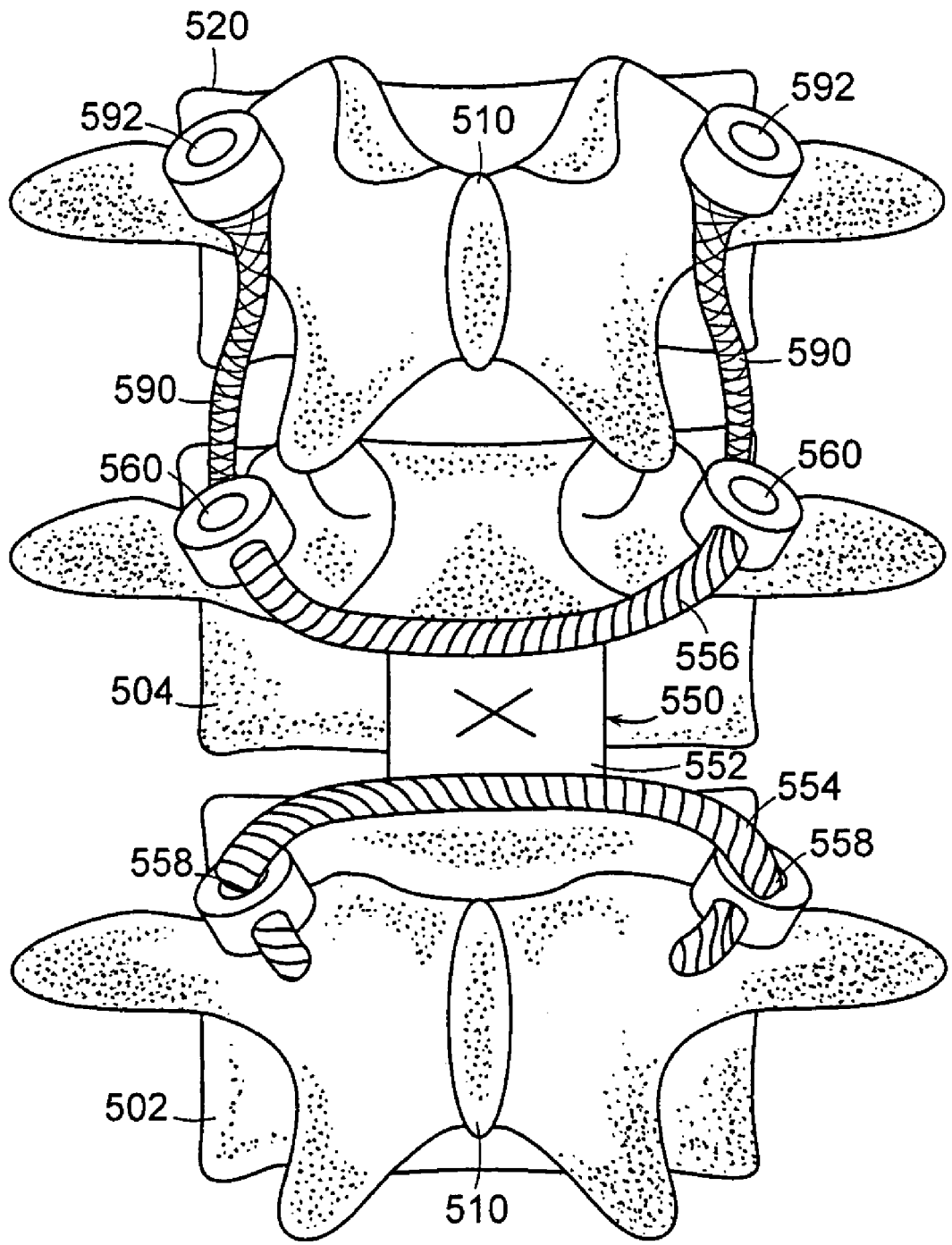
FIG. 5 depicts one embodiment of a device of the present invention.

FIG. 5 depicts one embodiment of a device of the present invention. Similar to FIG. 4B, three sequential vertebrae, 502, 504 and 520, are shown in a patient following a facetectomy between vertebrae 502 and 504 and laminectomy on vertebra 504. The device of the present invention comprises artificial facet joint 550. Artificial facet joint 550 has been implanted between vertebrae 502 and 504. The device of the present invention further includes artificial ligaments 590.

Artificial facet joint 550 represents a generic artificial facet joint that require removal of at least a portion spinous process 510 of vertebra 504 as represented by "X". In the embodiment shown in FIG. 5, the entire spinous process of 510 of vertebra 504 is removed by laminectomy and facetectomy. Artificial facet joint 550 restore the function of resected anatomy between vertebrae 502 and 504, including facet joints 508, capsulary ligaments, interspinous ligament, and supraspinous ligament. However, resection of spinous process 510 of vertebra 504 also removes at a portion of ligamentous connection between vertebrae 504 and 520, including interspinous ligament and supraspinous ligament between vertebrae 504 and 520. Therefore, artificial ligament 590 restores the function of the resected ligaments between vertebrae 504 and 520.

In one embodiment, artificial facet joint 550 includes coupling member 552. Referring to the embodiment shown in FIG. 5, artificial facet joint 550 includes connectors 554 and 556. Connector 554 connects coupling member 552 to vertebra 502 using pedicle screws 558. Connector 556 connects coupling member 552 to vertebra 504 using pedicle screws 560.

In the embodiment shown in FIG. 5, vertebra 520 is disposed adjacent and superior to vertebra 504, following facetectomy and laminectomy. Artificial ligaments 590 connect vertebrae 504 and 520. In one embodiment, artificial ligaments 590 are attached to vertebra 520 by pedicle screws 592. The other ends of the artificial ligaments 590 are attached by pedicle screws 560 that are the same pedicle screws used to attach artificial facet joints 550. Although pedicle screws 592 are used to attach artificial ligaments 590 to vertebra 520, artificial ligaments 590 may attach to other bony anatomy on vertebra 520 directly or indirectly using another mechanism. As non-limiting examples, artificial ligaments 590 can attach to vertebra 520 at vertebral body, pedicle, lamina, spinous process, transverse process, superior articular process, or inferior articular process. Moreover, artificial ligaments 590 mat not attach directly on vertebra 520, but it may wrap around any bony protrusion in vertebra 520 with or without any aid of another component such as a hook. Various means of attachment are discussed later. The opposite ends artificial ligaments 590 can also attach or wrap to various site on vertebra 504 similar to vertebra 520. Furthermore, artificial ligaments 590 may attach to vertebra 504 indirectly through the artificial facet joint 550. Again, as non-limiting examples, same attachment mechanism such as bone screws can be used to attach both artificial facet joint 550 and artificial ligaments 590, or artificial ligaments 590 may attach to any part of artificial facet join 550, including the connector 556. Any of the currently used artificial facet joints can be used as components of the device of the present invention. In one embodiment, an artificial facet joint described in the U.S. Pub. App. No. 2005/0055096 is used. Other embodiments include those described in U.S. Pat. Nos. 6,419,703, 6,565,605, 6,579,319, 6,610,091, 6,669,729, 6,902,580 and U.S. Pub. App. Nos. 2003/0004572, 2003/0028250, 2003/0040797, 2004/0006391, 2004/0049281, 2004/0049278, 2004/0049277, 2004/0049276, 2004/0049275, 2004/0049274, 2004/0049273, 2004/0049272, 2004/0111154, 2004/0254575, 2005/0027361, 2005/0033434, 2005/0085912, 2005/0102028, 2005/0119748. The entire teachings of these patents and published applications are herein incorporated by reference. Other examples of suitable artificial facet joints are described in U.S. Ser. Nos. 10/905,374 and 11/171,022, the teachings of which are incorporated herein in their entirety.

Figure 6:
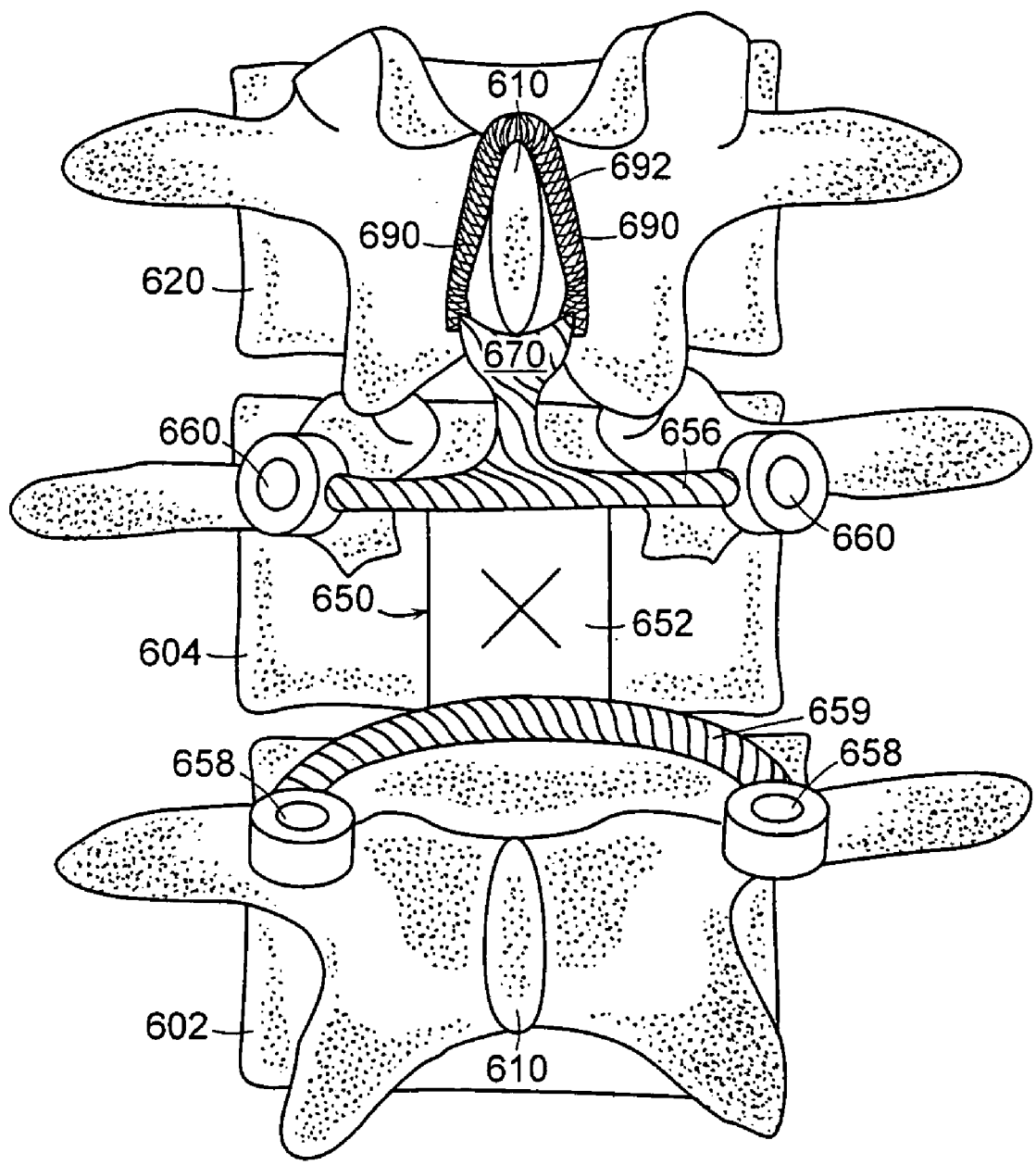
FIG. 6 depicts one embodiment of a device of the present invention.

Referring to FIG. 6, an embodiment of the present invention is shown. Three sequential vertebrae, 602, 604 and 620, are shown in a patient following facetectomy between vertebra 602 and 604 and laminectomy on vertebra 604. Artificial facet joint 650 has been implanted. Artificial facet joint 650 includes coupling member 652. Connectors 654 and 656 connect coupling member 652 to vertebrae 602 and 604 using pedicle screws 658 and 660. Artificial facet joint 650 further includes spinous process support 670. Spinous process support 670 further contributes to restoration of natural function of the functional spinal units comprising vertebrae 602 and 604 and vertebrae 604 and 620 by supporting spinous process 610 of vertebra 620. Artificial ligaments 690 are attached to spinous process support 670. In the embodiment shown in FIG. 6, artificial ligaments 690 are attached to spinous process 610 using spinous process hook 692. Therefore, vertebrae 604 and 620 are connected by the artificial ligaments 690.

Figure 7:
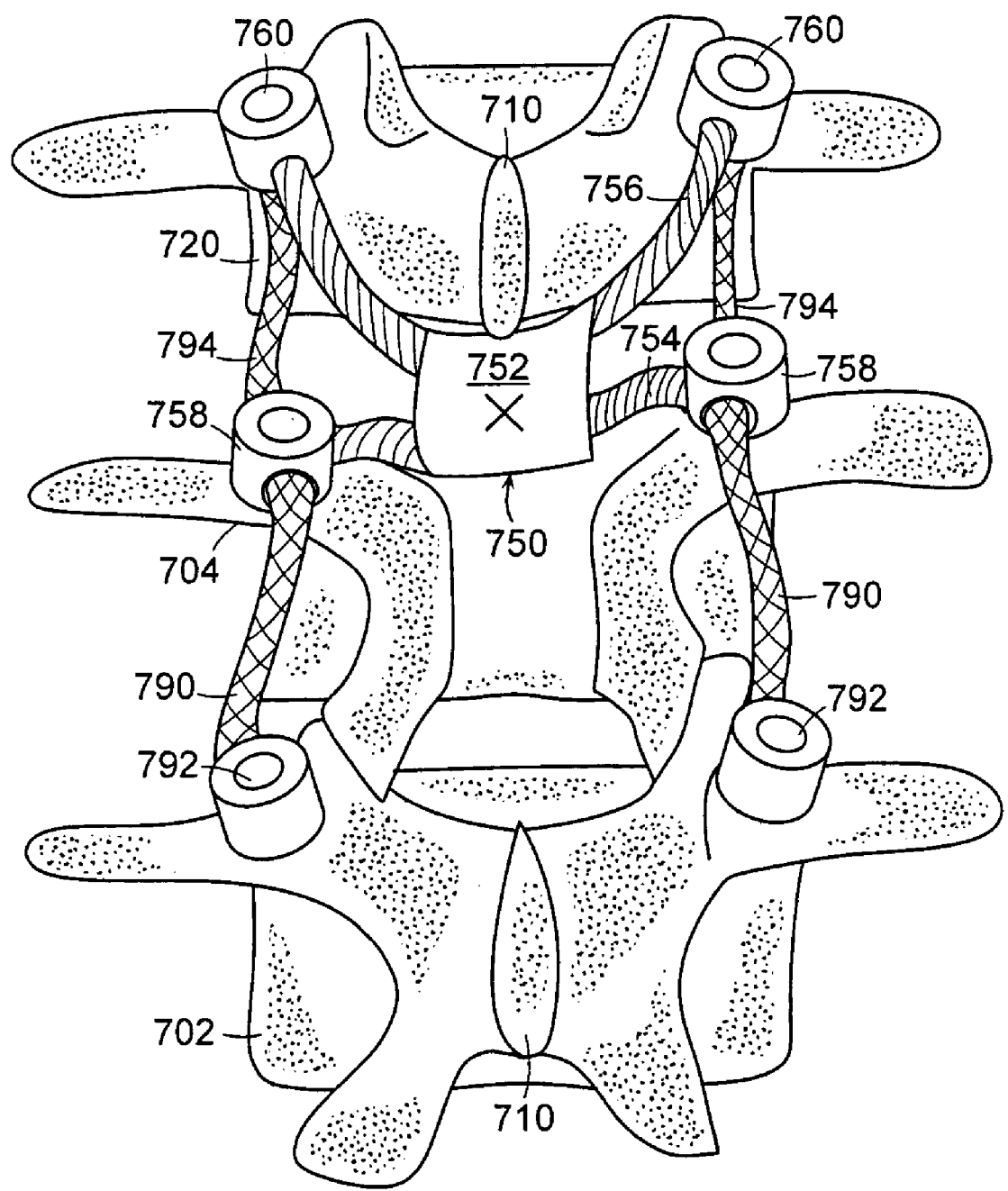
FIG. 7 depicts an alternative embodiment of a device of the present invention.

Referring to FIG. 7, an alternative embodiment of a device of the present invention is shown. Three sequential vertebrae, 702, 704 and 720, are shown in a patient following facetectomy between vertebra 704 and 720 and laminectomy on vertebra 704. An embodiment of artificial facet joint 750 has been implanted. Artificial facet joint 750 includes coupling member 752. Connectors 754 and 756 of facet joint 750 connect support member 752 to vertebrae 704 and 720 using pedicle screws 758 and 760. The device of the present invention further includes artificial ligaments 790 that connect vertebrae 702 and 704. Artificial ligaments 790 are attached to vertebra 702 by pedicle screws 792. The other ends of the artificial ligaments 790 are attached by pedicle screws 750 that are the same bone screws used to attach artificial facet joints 750. In the embodiment shown in FIG. 7, vertebra 702 is adjacent and inferior to vertebra 704, and vertebra 704 has received facetectomy of the superior facet joint, and laminectomy. Further, the embodiment of artificial facet joint 750 of the device shown in FIG. 7 includes additional artificial ligaments 794 that connects vertebrae 704 and 720. In this embodiment, artificial ligaments 794 are attached to pedicle screws 758 and 760. Additional artificial ligaments 794 additionally restores function lost by facetectomy and resection of the posterior spinal ligaments between vertebrae 704 and 720, including capsulary ligaments interspinous ligaments and supraspinous ligaments.

Figure 8A:
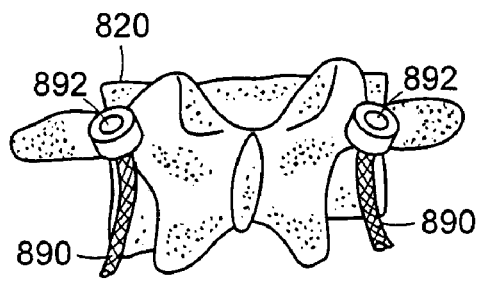
FIGS. 8A through 8E depict alternative embodiments of the attachment means that can be employed as components of the device of the present invention to vertebrae.
Figure 8B:
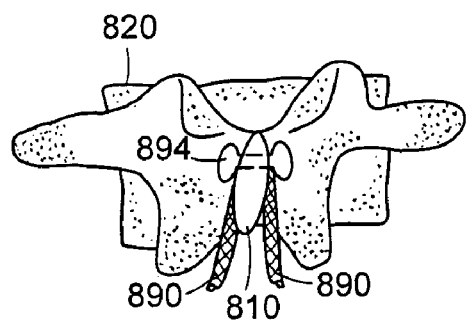
Figure 8C:
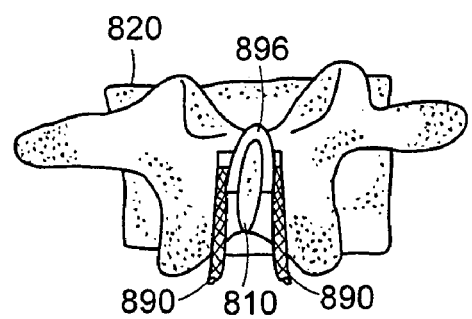
Figure 8D:
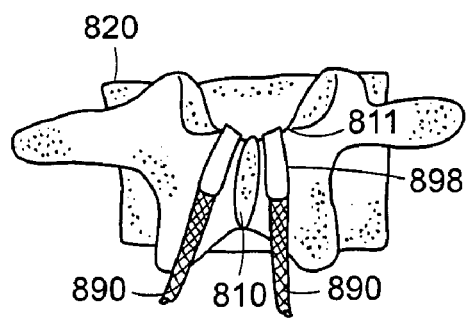
Figure 8E:
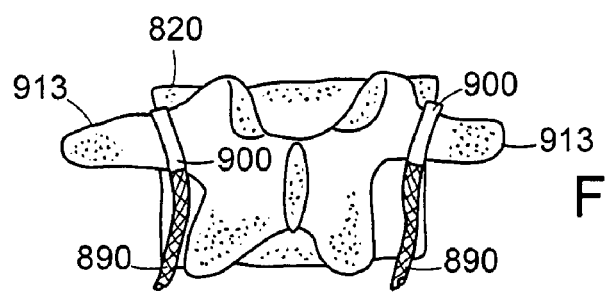

FIGS. 8A through 8E show additional examples of the attachment means that can be employed to attach artificial ligaments 890 of the device of the present invention to vertebra 820. The attachment mechanism listed in FIGS. 8A and 8E are not exhaustive, and a person skilled in the art will recognize that additional attachment mechanism can be used. Variety of bone screws, hooks, rivets, wires, and cables can be employed to secure the artificial ligaments to the vertebra or wrap the artificial ligaments around the vertebra. FIG. 8A shows bone screws 892, attachable to pedicles. FIG. 8B shows bone screw or bone rivet 894, attachable to spinous process 810. FIG. 8C shows spinous process hook 896, attachable to spinous process 810. FIG. 8D shows laminar hooks 898, attachable to lamina 811. FIG. 8E shows transverse process hooks 900 attachable to transverse processes 913.

Coupling member(s) and connectors of an artificial facet joint of the device of the present invention can be rigid or flexible. In one embodiment, the coupling members and the connectors are flexible. In another embodiment, the connectors are substantially rigid rods. Each flexible member can have a variety of configurations, shapes, and sizes. Coupling members can be formed from a wide range of biocompatible materials. Coupling members, in one embodiment, are formed from a polymer, and more preferably a biocompatible polymer, such as polyurethane, composite reinforced polyurethane, silicone, etc. Connecting members can be produced from such materials as metals, ceramics, polymers, etc.

Artificial ligaments of a device of the present invention perform a function of any combination of natural interspinous ligament, supraspinous ligament, and facet joint capsulary ligament. Therefore, artificial ligaments should have tensile strength of at least 50 N, preferably 100 N, more preferably 200 N. When extended with 200 N load, the ligament should produce at least 5% strain, preferably 10% strain, more preferably 30% strain. The artificial ligament should limit the flexion of a functional spinal unit to 15 degrees, preferably no more than 12 degrees of flexion.

In other embodiment, the flexible members may have no or low strain (less than 5% strain when loaded with 200 N). However, the ligament should be flexible to easily bend. When implanted, the ligament may be slack in the neutral position to allow flexion of a functional spinal unit to at least 6 degrees, preferably at least 12 degrees.

The artificial ligaments can be made of any biocompatible material including polyesters, polypropylene, polyethylene, carbon fiber, glass, glass fiber, polyurethane, plyaramide, metals, polymers, copolymers, polyactic acid (PLA), polyglycolic acid (PGA), silk, cellusoseic acid, polycaproactone fibers, or any combination of above. To increase the tensile strength multiple fibers can be weaved to form a band. Furthermore, in some embodiments, the flexible members may have time-dependent behavior such as creep. Thereby, the property of the artificial ligament changes over time. For example, the flexible member may be very stiff (e.g., allowing 5 degrees flexion) initially after implantation to protect the surrounding injured tissues and become more compliant due to creep as time progresses (e.g., allowing 10 degrees flexion after 3 months).

Furthermore, the artificial ligaments can be lubricated to lower the friction and wear between its fibers and/or between the ligament and surrounding structures (facet joint, bony structure, other soft tissues) using lubricants including hyaluronic acid, proteoglycans, and hydrogels. Finally, the artificial ligaments can be made of at least in part by subintestinal submucosa (SIS) to assist in the formulation of natural ligamentous tissue.

EQUIVALENTS

While this invention has been particularly shown and described with references to preferred embodiments thereof, it will be understood by those skilled in the art that various changes in form and details may be made therein without departing from the scope of the invention encompassed by the appended claims.

The invention claimed is:

1. An implantable device for stabilizing at least a portion of a spinal column, comprising:
   a) one or more implantable artificial facet joints, each of the said artificial facet joints configured to couple two or more adjacent vertebrae to restore function to one or more resected facet joints;
   b) one or more artificial ligaments configured to connect at least one vertebra coupled by one of the artificial facet joints to at least one additional vertebra not coupled by the artificial facet joint, each of the said additional vertebrae being adjacent to at least one of the vertebra coupled by the artificial facet joint, the one or more artificial ligaments being flexible to allow flexion of the additional vertebra relative to at least one of the vertebrae coupled by the artificial facet joint and to allow flexion of each of the vertebrae coupled by the artificial facet joint relative to at least one other of the vertebrae coupled by the artificial facet joint;
   c) one or more bone anchors coupled to at least one of the artificial ligaments for connecting the at least one artificial ligament to at least one of the vertebrae; and
   d) a connector that is attached to the artificial ligament, and which wraps around a portion of at least one of the vertebrae.

2. The device of claim 1, wherein at least one of the one or more implantable artificial facet joints couples two adjacent vertebrae.

3. The device of claim 2, wherein the additional vertebra not coupled by the artificial facet joint is superiorly adjacent to the superior of the two adjacent vertebrae coupled by the artificial facet joint.

4. The device of claim 2, wherein the additional vertebra not coupled by the artificial facet joint is inferiorly adjacent to the inferior of the two adjacent vertebrae coupled by the artificial facet joint.

5. The device of claim 1, wherein the one or more bone anchors includes at least one member selected from the group consisting of a screw, a rivet, a hook, a plate, a wire and a cable.

6. The device of claim 1, wherein the artificial ligament wraps around a portion of the referred vertebra.

7. The device of claim 1, further including a connector that is attached to the artificial ligament, and which wraps around a portion of at least one of the vertebrae.

8. The device of claim 1, wherein the at least one of the artificial ligaments wraps around at least one of the bone anchors which is attached to one of the vertebrae.

9. The device of claim 8, further including a connector attached to the artificial ligament and wrapped around the at least one of the bone anchors, said at least one of the bone anchors being attached to one of the vertebrae.

10. The device of claim 1, wherein the artificial ligament is attached to the artificial facet joint.

11. The device of claim 1, further including a connector that connects the artificial ligament to the artificial facet joint.

12. The device of claim 1, wherein the artificial ligament and the artificial facet joint share an attachment to the vertebra.

13. The device of claim 1, further including a connector that is attached to the artificial ligament, and wherein the connector and the artificial joint share an attachment to one of the vertebrae.

14. The device of claim 1, wherein at least one of the artificial ligaments includes at least one terminal portion that is attachable to at least one pedicle of at least one vertebra by at least one pedicle screw.

15. The device of claim 1, wherein at least one of the artificial ligaments is connected to at least one of a bone rivet and a bone screw, the bone rivet or bone screw being attachable to a spinous process of at least one of the vertebrae.

16. The device of claim 1, wherein at least one of the artificial ligaments is connected to a spinous process hook that is attachable to the spinous process of the at least one vertebrae.

17. The device of claim 1, wherein at least one of the artificial ligaments includes at least one terminal portion attachable to a lamina of at least one of the vertebrae by at least one of a lamina hook and a bone screw.

18. The device of claim 1, wherein at least one of the artificial ligaments is connected to a transverse process hook that is attachable to a transverse process of at least one of the vertebrae.

19. The device of claim 1, further including at least one artificial ligament that connects at least two vertebrae coupled by at least one of the artificial facet joints.

20. The device of claim 1, wherein at least one of the implantable artificial facet joints further includes:
   a) one or more coupling members, said coupling members configured to couple two or more adjacent vertebrae; and
   b) at least one connector for each vertebra coupled to the artificial facet joints, wherein each connector is configured to connect the said vertebra to one or more coupling members.

21. The device of claim 20, including at least one additional artificial ligament, wherein each additional ligament includes two terminal ends, and wherein at least one terminal end of each of the additional artificial ligaments is each attached to at least one said connector.

22. The device of claim 20, wherein the artificial facet joint further includes a spinous process supporting member that supports a spinous process of the additional vertebra that is not coupled by the artificial facet joint, and wherein at least one artificial ligament connects the spinous process supporting member to the spinous process of the additional vertebra.

23. The device of claim 22, wherein the spinous process supporting member and the connector are substantially rigid.

24. The device of claim 22, wherein the spinous process supporting member and the connector are flexible.

25. The device of claim 20, wherein the connectors are substantially rigid rods.

26. The device of claim 20, wherein the connectors include terminal portions attachable to the pedicles of the corresponding vertebra, by pedicle screws.

* * * * *